(12) United States Patent
Karge et al.

(10) Patent No.: US 8,658,793 B2
(45) Date of Patent: Feb. 25, 2014

(54) PROCESS FOR THE PREPARATION OF PYRIMIDINE DERIVATIVES

(71) Applicant: DSM IP Assets B.V., Heerlen (NL)

(72) Inventors: Reinhard Karge, Staufen (DE); Jan Schultz, Lorrach (DE)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/893,114

(22) Filed: May 13, 2013

(65) Prior Publication Data

US 2013/0245263 A1    Sep. 19, 2013

Related U.S. Application Data

(63) Continuation of application No. 13/263,142, filed as application No. PCT/EP2010/054629 on Apr. 8, 2010, now Pat. No. 8,461,168.

(30) Foreign Application Priority Data

Apr. 8, 2009    (EP) .................................... 09157590

(51) Int. Cl.
    *C07D 239/02*    (2006.01)
(52) U.S. Cl.
    USPC ........................................................ 544/329
(58) Field of Classification Search
    USPC ........................................................ 544/329
    See application file for complete search history.

(56) References Cited

U.S. PATENT DOCUMENTS

| | | | |
|---|---|---|---|
| 2,235,638 A | 3/1941 | Otto | |
| 3,226,424 A | 12/1965 | Mischa et al. | |
| 3,966,791 A | 6/1976 | Leimgruber et al. | |
| 3,985,785 A * | 10/1976 | Edenhofer et al. | 558/446 |

FOREIGN PATENT DOCUMENTS

| | | |
|---|---|---|
| DE | 25 36 950 | 3/1976 |
| EP | 1 184 369 | 3/2002 |

OTHER PUBLICATIONS

D. J. Brown et al., 28 Australian Journal of Chemistry, 119-127 (1975).*
Ershov et al., 20 Chemistry of Heterocyclic Compounds, 439-443 (1984).*
International Search Report for PCT/EP2010/054629, mailed Aug. 23, 2011.
L.V. Ershov et al., "Acetals of lactams and acid amides. 41. Enamino amides in the synthesis of pyrimidine derivatives", *Chemistry of Heterocyclic Compounds*, vol. 20, No. 4, Apr. 1984, pp. 439-443.
L.V. Ershov et al, 20 Chemistry of Heterocyclic Compounds, 439-443 (1984).
D.J. Brown et al, 28 Australian Journal of Chemistry, 119-127 (1975).
Ryndina et al, Torp-Ziegler Cyclization in the Synthesis of 3-Amino-4-Cyanopyrrole Derivatives, Chemistry of Heterocyclic Compounds, vol. 36, No. 12, 2000.

* cited by examiner

*Primary Examiner* — James O Wilson
*Assistant Examiner* — Alexander R Pagano
(74) *Attorney, Agent, or Firm* — Nixon & Vanderhye P.C.

(57) ABSTRACT

A process for the preparation of 5-substituted 4-amino-2-methylpyrimidines of the formula

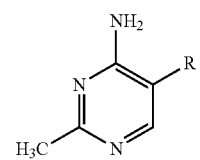

wherein R is $CONH_2$ or CN, and of acid addition salts thereof, characterized in that a compound of formula $H_2N-CH=C(R)CN$ (II) is reacted with acetimidic acid methyl ester or an acid addition salt thereof and that, if desired, a compound of formula I is transferred into an acid addition salt, and the transformation of a compound of formula II wherein R is $CONH_2$ into a compound of formula II wherein R is CN by treatment with $POCl_3$.

1 Claim, No Drawings

PROCESS FOR THE PREPARATION OF PYRIMIDINE DERIVATIVES

This application is a continuation of commonly owned copending U.S. Ser. No. 13/263,142, filed Dec. 23, 2011 (U.S. Pat. No. 8,461,168), which is the national phase application of international application PCT/EP2010/054629, filed Apr. 8, 2010 which designated the U.S. and claims benefit of EP 09157590.2, dated Apr. 8, 2009, the entire contents of each of which are hereby incorporated by reference.

The present invention relates to the preparation of pyrimidine derivatives. More precisely, the present invention relates to the preparation of 5-substituted 4-amino-2-methylpyrimidines of the formula

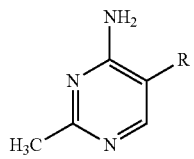

I wherein R is $CONH_2$ or CN,
and of their acid addition salts.

The compounds of formula I and their acid addition salts are known compounds and intermediates in processes for the preparation of vitamin $B_1$ (thiamin) comprising a thiazole and a pyrimidine. One general approach for the synthesis of thiamine is the separate synthesis of the thiazole and the pyrimidine building blocks followed by their condensation reaction. This method was originally reported by Williams, R. R., et al. (J. Am. Chem. Soc. 58, 1504 [1936]). An alternative general method builds the thiazole ring on a preformed pyrimidine intermediate. Currently all industrial production processes use this approach which proceeds via the key intermediate 4-amino-5-aminomethyl-2-methylpyrimidine (also called Grewe diamine). The aminomethyl side chain is extended by 3-chloro-5-hydroxypentane-2-one, 3-mercaptoketone or their corresponding acetates and cyclized to the thiazole ring.

In this approach in the majority of cases malononitrile is used as starting material for the construction of the pyrimidine ring. Malononitrile again can be obtained by addition of ammonia to acrylonitrile and subjecting the β-aminopropionitrile to oxidative dehydrogenation in the gas phase at high temperature and in the presence of molecular oxygen and a metallic catalyst (Ullmann's Encyclopedia of Industrial Chemistry, 5$^{th}$ ed., Vol. 27A, 515-517).

Since malononitril is a very cost intensive starting material for the industrial synthesis of vitamin $B_1$ it was an objective to find more appropriate substitutes for it. This problem has been solved by using a compound of formula $H_2H$—CH=C(R)—CN (II) wherein R is $CONH_2$ or CN in a cyclisation with acetimidic acid methylester of formula $H_3C$—C(=NH)—$OCH_3$ (III) to form the 4-amino-2-methylpyrimidine ring of vitamin $B_1$.

The present invention, therefore, relates to a process for the preparation of 5-substituted 4-amino-2-methylpyrimidines of the formula

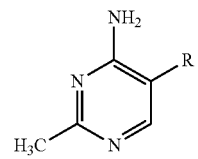

I wherein R is $CONH_2$ or CN,
and of acid addition salts thereof, characterized in that a compound of formula $H_2N$—CH=C(R)—CN (II) is reacted with acetimidic acid methyl ester ($H_3C$—C(=NH)—O—$CH_3$) or an acid addition salt thereof and that, if desired, a compound of formula I is transferred into an acid addition salt.

The reaction can be carried out without a solvent or in solution. It is conveniently conducted in an inert, polar solvent, such as an aliphatic alcohol, preferably with 1-8 C-atoms, more preferably with 1-4 C-atoms, at a temperature in the range of −10 to 100° C., preferably 0-60° C. and under a pressure of 1-10 bar, preferably 1-5 bar, if desired under an inert gas. Normally the reaction is complete after 12 hours up to 24 hours.

Acid addition salts of compounds of formula (I) with organic or, norganic acids are obtained if the reaction is carried out under corresponding acidic conditions or if a corresponding acid is added after the reaction. Preferred acid addition salts are the salts with hydrohalide acids; most preferred is the hydrochloride.

The 3-amino-2-cyanoacrylamid starting material is a known material and can be obtained from formamidine and cyanoacetimide as described, e.g., in U.S. Pat. No. 3,487,083.

Acetimidic acid methyl ester is also a known compound which is commercially available and can be prepared, e.g., as described in EP 1 840 118 A1.

The transformation of 4-amino-2-methyl-5-pyrimidinecarboxamide into 4-amino-2-methyl-5-pyrimidinecarbonitril with $POCl_3$ by intramolecular dehydration is known, e.g., from J. Chem. Soc. 1937, 364 (Todd et. al.), although with yields only up to 50%. Own experiments to increase the yield in this reaction by variation of the reaction conditions failed. On the other hand intramolecular dehydration of 3-amino-2-cyanoacrylamide with $POCl_3$ to 2-aminomethylene-malononitrile has so far not been described in the literature and was achieved with a yield of 79.4% and a purity of 42.6% which result is surprising, particularly since with $COCl_2$ no dehydration was achieved.

Therefore, this reaction is also part of the invention.

The dehydration reaction is conveniently carried out in solution, preferably in a polar solvent, such as dimethyl formamide, dimethyl acetamide or dimethoxy-ethane, at a temperature in the range of from −10° C. to 100° C., preferably from 0-60° C., under a pressure in the range of 1-10 bar, preferably 1-5 bar and preferably in the presence of a base, e.g., an aromatic or aliphatic amine, such as pyridine or $NR_3$ (wherein $R_3$ is $C_{1-4}$-alkyl), most preferably triethylamine. Normally the reaction is complete after 12 hours up to 24 hours.

It is interesting to note that while the cyclization of 2-aminomethylene-malononitril to 4-amino-2-methyl-5-cyanopyrimidine with acetimidic acid methyl ester under the reaction conditions of the present invention is achieved with a yield of 60% and a puritiy of 64.8% no cyclization is achieved with acetimidine, demonstrating that acetimidine and acetimidic acid methyl ester cannot be regarded as being equivalent in the cyclisation of compounds II to compounds I.

The following examples illustrate the present invention in more detail.

EXAMPLE 1

1.85 g of acetamidic acid methyl ester hydrochloride (95.0%, 16.07 mmol) and 2.0 g of 3-amino-2-cyano-acrylamide (68.7%, 12.36 mmol) were suspended in 20 ml of methanol. 2.89 g NaOMe (30%, 16.07 mmol) were added and the suspension was heated to 45° C. under stirring for 24 hours. No conversion was observed. The reaction mixture was then heated to 70° C. under stirring for 3.5 hours. After addition of 1.15 ml of NaOMe methanol (30%) heating to 70° C. under stirring was continued for 3 hours. The reaction mixture was filtered and the filter cake was dried under 30 mbar/50° C. The yield of 4-amino-2-methyl-5-pyrimidinecarboxamide was 2.25 g (purity 30.1%). The mother liquor was concentrated under 30 mbar/50° C. and yielded a further 1.0 g of the product (purity 12.3%). Total yield: 42.5%.

EXAMPLE 2

To a mixture of 0.60 g of 3 amino-2-cyano-acrylamide (82.2%, 4.44 mmol) and 20 ml of dimethoxyethane 0.56 g of triethylamine (99.5%, 5.52 mmol) was added at room temperature. Then 0.56 g of $POCl_3$ (98.0%, 3.55 mmol) was added dropwise. The suspension turned yellow and after 5 hours all volatiles were removed under 30 mbar/42° C. 780 mg of 2-aminomethylene-malononitrile were obtained.

Yield: 79.4%; purity 42.6%. A higher purity can be reached by extraction of the product in aqueous NaOH (28%) with dichloromethane.

EXAMPLE 3

27.97 g of NaOMe in methanol (13.72 mmol, 2.7%) were added to 1.58 g of acetimidic acid methylester hydrochloride (95.0%, 13.72 mmol) and 1.43 g of 2-aminomethylene-malononitrile (68.7%, 10.55 mmol) and the mixture was stirred for 5 hours at room temperature under argon. While the 4-amino-2-methyl-5-pyrimidinecarbonitril did not precipitate even with addition of sodium chloride and cooling to 0° C. work-up was achieved by removing all volatiles under 30 mbar/48° C. The remaining solids were suspended in water and filtered. The filter cake was dried and analyzed by NMR. Yield of pyrimidinecarbonitril: 1.33 g (60.0%, purity 64.8%).

EXAMPLE 4

To a mixture of 0.68 g of 3-amino-2-cyanoacrylamide (82.2%, 5.03 mmol) and 10 ml of dimethoxyethane 0.63 g of triethylamine (99.5%, 6.26 mmol) were added. Then 0.63 g of $POCl_3$ (98.0%, 4.02 mmol) were added dropwise upon which the suspension turned brownish. After two hours of stirring at room temperature there were still 20% of starting material left. Additional $POCl_3$ (0.17 ml) was added dropwise. After three hours all volatiles were removed at 30 mbar, 40° C. The remaining solid residue was dissolved in 10 ml of methanol and 0.75 g of acetimidic acid methylester hydrochloride (95.0%, 6.54 mmol) was added. Then 13.33 g of NaOMe in methanol (2.7%, 6.54 mmol) were added and the mixture was stirred for 18 hours at 45° C. Only 2-aminomethylene-malononitrile was found, no pyrimidinecarbonitrile.

EXAMPLE 5

To a mixture of 0.41 g of 2-aminomethylene-malononitrile (4.44 mmol) in 10 ml of isopropanol a solution of 2.74 g of acetamidine in isopropanol (9.9%, 4.66 mmol) was slowly added. After stirring the suspension for four hours at room temperature no pyrimidinecarbonitril was detected in the reaction mixture.

The invention claimed is:

1. A process for the preparation of 5-substituted 4-amino-2-methylpyrimidine of the formula

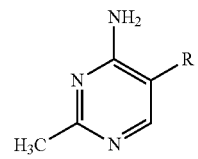

I wherein R is $CONH_2$,
and acid addition salts thereof, wherein the process comprises reacting a compound of formula $H_2N$—$CH$═$C(R)$—$CN$ (II) with acetimidic acid methyl ester or an acid addition salt thereof or, optionally, transferring a compound of formula I into an acid addition salt.

* * * * *